United States Patent [19]

Smith

[11] Patent Number: 5,783,698

[45] Date of Patent: Jul. 21, 1998

[54] CHEMICAL SYNTHESIS OF 1,3-DISUBSTITUTED QUINAZOLINEDIONES

[75] Inventor: Adrian Leonard Smith, Bishops Stortford, United Kingdom

[73] Assignee: Merck Sharp & Dohme Limited, Hoddesdon, United Kingdom

[21] Appl. No.: 779,498

[22] Filed: Jan. 7, 1997

[30] Foreign Application Priority Data

Jan. 23, 1996 [GB] United Kingdom ............ 9601293

[51] Int. Cl.$^6$ .................................................. C07D 239/54
[52] U.S. Cl. ........................................ 544/285; 514/259
[58] Field of Search ......................................... 544/285

[56] References Cited

U.S. PATENT DOCUMENTS

| | | | |
|---|---|---|---|
| 3,681,352 | 8/1972 | Rosenfeld et al. | 544/285 |
| 3,882,121 | 5/1975 | Cohen et al. | 544/285 |
| 5,384,405 | 1/1995 | Hani et al. | 544/285 |
| 5,539,114 | 7/1996 | Cosmo et al. | 544/285 |

OTHER PUBLICATIONS

Janssen et al., Journal of Labelled Compounds and Radiopharmaceuticals, vol. XXV, No. 7, pp. 783–792, Jul. 1988.
Nomoto et al., Chemical Pharmaceutical Bulleting, 39(4), 900–910, 1981, Apr. 1991.

*Primary Examiner*—Matthew V. Grumbling
*Attorney, Agent, or Firm*—J. Eric Thies; David L. Rose

[57] ABSTRACT

The present invention relates to a method for the synthesis of 1,3-disubstituted quinazolinedione derivatives which comprises:

(a) reacting a haloformate functionalized polystyrene resin with a substituted anthranilic acid derivative under conditions effective to form a urethane-linkage;

(b) reacting the product of step (a) with a primary amine under conditions effective to form an anthranilamide derivative;

(c) heating the anthranilamide to effect intramolecular cyclization thereby liberating the 1,3-disubstituted quinazolinedione derivative from the resin into solution; and (d) isolating the 1,3-disubstituted quinazolinedione by filtration and solvent removal.

7 Claims, No Drawings

CHEMICAL SYNTHESIS OF 1,3-DISUBSTITUTED QUINAZOLINEDIONES

The present invention relates to the field of solid phase synthetic chemistry. More particularly, the present invention provides a solid phase synthetic route for the preparation of the quinazolinedione template and a corresponding combinatorial library.

In recent years there has been an explosion of interest in the synthesis and screening of combinatorial libraries for lead generation in the drug discovery process (for reviews see, for instance, M. A. Gallop et al. *J. Med. Chem.*, (1994) 37(9), 1233–1252; and E. M. Gordon et al, *J. Med. Chem.*, (1994) 37(10), 1386–1401). Whilst much of the early work was devoted to the synthesis of peptide and peptoid libraries, there is an increasing realization that 'small molecule' libraries based upon heterocyclic templates are more likely to produce quality leads with the physicochemical/pharmacokinetic properties necessary to make a drug. This is especially true when seeking molecules with activity in the central nervous system (CNS), where the highly polar nature of peptides/peptoids prevents them from easily crossing the blood-brain barrier. There has, however, been relatively little reported in the literature on the synthesis of template-based small molecule libraries, being restricted to benzodiazepines, (S. H. DeWitt et al, *Proc. Natl. Acad. Sci. U.S.A.*, (1993) 90, 6909–6913; B. A. Bunin and J. A. Ellman, *J. Am. Chem. Soc.*, (1992) 114, 10997–10998; and International Patent Specification No. WO 94/06291), hydantoins (S. H. DeWitt et al, supra), diketopiperazines (D. W. Gordon and J. Steele, *J. Biorg. Med. Chem. Lett.*, (1995) 5, 47–50) and thiazolidines (M. Patek et al, *Tetrahedron Lett.*, (1995) 36, 2227–2230).

The quinazolinedione template occurs in a large number of bioactive molecules including serotonergic, dopaminergic and adrenergic receptor ligands and inhibitors of aldose reductase, lipoxygenase, cyclooxygenase, collagenase and carbonic anhydrase. A combinatorial library based upon this template would therefore be expected to provide lead compounds in a wide range of bioassays.

Experimentation with existing solution phase methods for the synthesis of 1,3-disubstituted quinazolinediones (see, for instance, R. L. Jacobs, *J. Heterocyl. Chem.*, (1990) 7, 1337–1345; S. M. Gradekar et al, *J. Chem. Soc.*, (1946) 4666–4668; B. Taub et al, (1961) 26, 5238–5239; and R. Cortez et al *Synthetic Commun.*, (1991) 21, 285–292), revealed serious shortcomings when trying to adapt them to solid phase. Particular problems were encountered with the ambident nucleophilicity of anthranilamide systems (e.g. O- rather than N-acylation) which resulted in unpredictable results. The present invention provides a new approach to the construction of the quinazolinedione template which is experimentally very simple, reliable and efficient, and which is suitable for the solid phase construction of combinatorial libraries.

An object of the present invention, therefore, is to provide a solid phase synthetic approach to 1,3-disubstituted quinazolinediones which does not leave an extraneous polar resin-tethering substituent on the resulting molecules which might compromise CNS penetration. In a further object, the present invention provides the incorporation of a wide variety of 1- and 3-substituents in the form of primary amines. Since there are approximately 8000 suitable commercially available primary amines, this provide considerable scope for structural diversity within a library.

Thus, in a first aspect of the present invention there is provided a method for the synthesis of 1,3-disubstituted quinazolinedione derivatives which comprises:

(a) reacting a haloformate functionalised polystyrene resin with a substituted anthranilic acid derivative under conditions effective to form a urethane-linkage;

(b) reacting the product of step (a) with a primary amine under conditions effective to form an anthranilamide derivative;

(c) heating the anthranilamide to effect intramolecular cyclisation thereby liberating the 1,3-disubstituted quinazolinedione derivative from the resin into solution; and (d) isolating the 1,3-disubstituted quinazolinedione by filtration and solvent removal.

The method of the present invention for the synthesis of 1,3-disubstituted quinazolinediones (1) is conveniently illustrated by the following scheme:

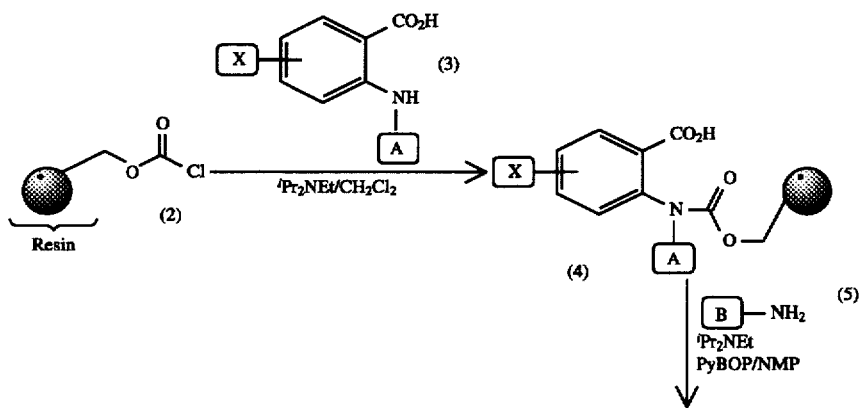

Scheme 1

-continued
Scheme 1

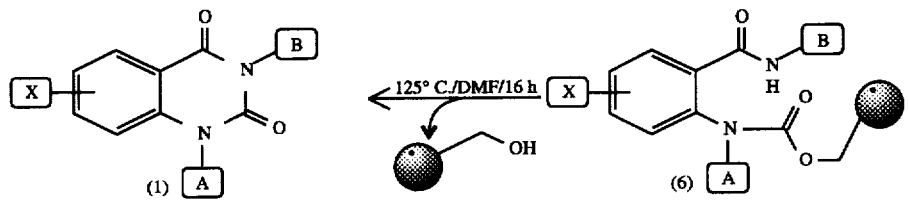

in which the following abbreviations are used
iPr₂NEt—N,N-diisopropylethylamine
CH₂Cl₂—dichloromethane
PyBOP—benzotriazole-1-yloxy-tris-pyrrolidino-phosphonium hexafluorophosphate
NMP—N-methylpyrrolidinone
DMF—N,N-dimethylformamide Preferably step (a) is effected at between 10° and 50° C., conveniently at room temperature. Suitable solvents include ethers, for example, tetrahydrofuran, or, more preferably, halogenated hydrocarbons, especially dichloromethane.

Step (b) may be effected in the presence of any peptide coupling reagent, in particular, bromo-tris-pyrrolidino-phosphonium hexafluorophosphate (PyBroP) or, more preferably, benzotriazole-1-yloxy-tris-pyrrolidino-phosphonium hexafluorophosphate (PyBOP). The exact choice of reaction conditions will be dependent upon the peptide coupling reagent used and will be readily apparent to those skilled in the art.

The cyclisation step (c) may be effected at between 80° and 200° C., preferably at about 125° C. Suitable solvents include, but are not restricted to, amides such as N,N-dimethylformamide.

With reference to Scheme 1, preferably, the haloformate functionalised polystyrene resin (2) is a chloroformate resin. Suitable resins are readily prepared by conventional functionalisation of commercially available resins, for example, TentaGel™-derived chloroformate resin. In a preferred aspect of the invention, a chloroformate functionalised polystyrene resin is used, which may be prepared immediately prior to use from aminomethyl polystyrene resin (loading: 1.0 mmol/g), triethylene-glycol bischloroformate (3 equiv.) and Hünig's base (3 equiv.) in dichloromethane at 20° C. for 1 hour.

Suitable primary amines (5) are readily available, for example, as listed in the Available Chemical Directory (Molecular Designs Lt., 2132, Farallon Drive, San Leandro, Calif. 94577).

With reference to Scheme 1, above, the chloroformate functionalized polystyrene resin (2) (loading: ~0.30 mmol/g) may be treated with a wide range of substituted anthranilic acids (3) (3 equiv.) in the presence of Hünig's base (CH₂Cl₂, 20° C., 1 hour) to give the urethane-linked system (4). Structurally diverse primary amines are double coupled to the free carboxylic acid using standard PyBOP conditions (2×1 hour) to give the anthranilamide (6). In the final key step of the synthesis, heating this system in DMF at 125° C. for 16 hours caused the amide nitrogen to shut down onto the urethane to generate the 1,3-disubstituted quinazolinedione template and simultaneously liberate the molecule from the resin into solution. Filtration and solvent removal then gives the final products lacking any extraneous tethering substituents. Since the molecule is only released into solution if all synthetic steps have worked, the products obtained are of very high purity (>95% in the vast majority of cases). The final cyclization/cleavage conditions are optimized for all combinations of A=methyl, phenyl, benzyl and B=phenyl, benzyl, chosen as a representative range of reactivities. Heating at 125° C. for 16 hours gave a uniform yield of 0.20 mmol/g for all six permutations of substituents, and purities in all cases were in excess of 95%.

Whilst there are approximately 50 commercially available anthranilic acids suitable for inclusion in a combinatorial library, much greater structural diversity is achieved if the A substituents is incorporated from primary amines. The procedure for the synthesis of anthranilic acids shown in Scheme 2 (based upon that described by S. T. Brennan et al, *J. Heterocycl. Chem.*, (1989) 26, 1469–1476) is ideal for this purpose since the pure anthranilic acid is almost invariably obtained simply by dilution of the reaction mixture with water, filtration, washing with acetone and ether, and drying. No subsequent purification is necessary. This means that a large number of reactions can be rapidly carried out in parallel.

Scheme 2

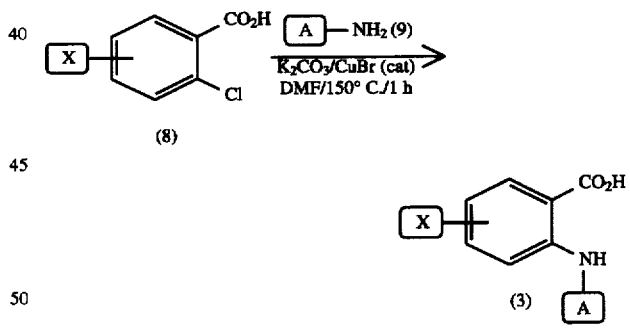

In a further aspect, the present invention provides for the construction of a number of combinatorial libraries based upon the quinazolinedione template using the resin-archived split/mix approach (see A. Furka et al, *Int. J. Pept. Protein Res.*, (1991) 37, 487–493) for the generation of combinatorial mixtures. A structurally diverse combinatorial library of 4000 compounds was synthesized using this methodology (50×anthranilic acids, 80×B substituents). Representative examples of the subunits used are shown in Table 1, and library construction details are given in the following examples.

TABLE 1

| Subunit | Anthranilic Acid (3) | Amine (5) |
|---|---|---|
| 1 | 2-aminobenzoic acid (HOOC, NH₂) | 2-amino-4-methoxyphenyl methyl ether (MeO, NH₂, OMe) |
| 2 | 2-amino-5-nitrobenzoic acid (HOOC, NH₂, O₂N) | tert-butyl (4-aminophenyl)carbamate |
| 3 | 2-amino-4,5,6-trimethoxybenzoic acid (HOOC, NH₂, MeO, OMe, OMe) | 3-methyl-5-amino-isothiazole (Me, NH₂, N—S) |
| 4 | 2-(phenylamino)benzoic acid (HOOC, NH-Ph) | 1-(3-aminopropyl)imidazole |
| 5 | 4-bromo-2-((pyridin-3-ylmethyl)amino)benzoic acid (HOOC, NH-CH₂-pyridyl, Br) | 3-methoxy-4-hydroxy-5-methoxyphenethylamine (MeO, HO, OMe, NH₂) |
| 6 | 2-((4-methoxyphenyl)amino)-5-nitrobenzoic acid (HOOC, NH-Ar-OMe, O₂N) | 2-(2-aminoethoxy)ethanol (HO-CH₂CH₂-O-CH₂CH₂-NH₂) |
| 7 | 2-((3-nitrophenyl)amino)benzoic acid (HOOC, NH-Ar-NO₂) | 2-aminobenzylamine (NH₂, CH₂NH₂) |
| 8 | 2-((dimethylaminomethyleneamino-methylene)amino)benzoic acid (HOOC, NH-CH=N-N(Me)=CH-Me) | furfurylamine (furan-CH₂-NH₂) |

Further modifications of (6) prior to cyclization/cleavage are possible to synthesize larger libraries, for example by addition of extra subunits to A, B and X, making this an extremely practical and versatile method for the construction of a combinatorial library.

In the following specific examples, $^1$H NMR spectra were recorded on a Bruker AM-360 spectrometer. $^1$H Chemical shifts are reported in ppm referenced to tetramethylsilane (TMS). Mass spectra were obtained on a VG Quattro instrument using electrospray chemical ionization. High resolution mass spectra were obtained by negative ion SIMS on a VG AutoSpecE mass spectrometer by M-Scan Ltd, Ascot, UK. Melting points (uncorrected) were determined using a Reichert Thermovar hot stage microscope. Reversed phase analytical HPLC was performed on an HP-1090 HPLC using gradient elution 5% to 95% MeCN in pH 3 aqueous phosphate buffer. Microanalyses were performed by Butterworth laboratories Ltd, Middlesex, UK. Aminomethyl polystyrene resin was purchased from Rapp Polymere and triethyleneglycol bischloroformate was purchased from Carbolabs. Subunits were purchased from suppliers listed in the Available Chemical Directory (MDL, San Leandro, Calif. 94577). Reactions were carried out using commercially available anhydrous solvents.

4-Chloro-2-(3-pyridylmethylamino)benzoic acid

A mixture of 2,4-dichlorobenzoic acid (10 g, 53 mmol), 3-aminomethylpyridine (4.5 ml, 44 mmol), $K_2CO_3$ (7.8g, 56 mmol) and CuBr (80 mg, cat) in DMF (20 ml) was heated at 150° C. for 1 hour, cooled to 0° C., diluted with water (80 ml) and carefully acidified with glacial acetic acid. The resulting solid was collected by filtration, washed with water, acetone and ether to give the pure product (>99% by HPLC) as a bluish white solid (3.46 g, 30%), m.p. 235°–236° C.; $^1$H NMR d (DMSO, 360 MHz, 353 K) 8.60 (bs, 1H, aromatic), 8.49 (bs, 1H, aromatic), 7.79 (d, J=8.5 Hz, 1H, aromatic), 7.72 (d, J=7.8 Hz, 1H, aromatic), 7.35 (dd, J=4.8, 7.6 Hz, 1H, aromatic), 6.74 (d, J=1.8 Hz, 1H, aromatic), 6.59 (dd, J=2.0, 8.4 Hz, 1H, aromatic), 4.51 (s, 2H, $CH_2$); HRMS [M-2H]$^-$ calcd for $C_{13}H_9N_2O_2Cl$: 260.0353. Found: 260.0348. Anal. calcd for $C_{13}H_{11}ClN_2O^2 \cdot \frac{1}{4} H_2O$: C, 58.44; H, 4.33; N, 10.48. Found: C, 58.30; H, 4.10; N, 10.25.

Synthesis of quinazolinedione combinatorial library

An isopycnic slurry of 110 g aminomethyl polystyrene resin (loading 1.0 mmol N/g) in DMF/$CH_2Cl_2$ (1.1 liter) was evenly distributed between 55×25 ml solid phase reaction vessels. Each vessel was drained, washed with $CH_2Cl_2$ (5×10 ml), suspended in $CH_2Cl_2$ (10 ml) and triethyleneglycol bischloroformate (1.6 ml, 8 mmol) was added. The reaction vessels were agitated for 15 min, and then Hünig's base (0.52 ml, 3 mmol) was added to each. The reaction vessels were agitated for a further 1 hour, drained, and washed with $CH_2Cl_2$ (2×10 ml). A solution of the anthranilic acid (3) (6 mmol) and Hünig's base (2 ml, 12 mmol) in $CH_2Cl_2$ (10 ml) was added to the reaction vessel (a different anthranilic acid to each) and the reaction vessels were agitated for 2 hours. The vessels were drained, washed with $CH_2Cl_2$ (3×10 ml), MeOH (2×10 ml) and $Et_2O$ (2×10 ml) and dried under vacuum.

50 mg of each resin was transferred to individual 6 ml solid phase reaction vessels, washed with N-methylpyrrolidinone (NMP) (5×1 ml), and a solution of 0.2 mmol $PhCH_2NH_2$ and Hünig's base (0.5 mmol) in NMP (0.5 ml) was added to each followed by 0.4M PyBOP in NMP (0.5 ml). The reaction vessels were agitated for 1 hour, drained, and a double coupling performed. The reaction vessels were washed with DMF (5×1 ml), the resin was suspended in DMF (1 ml), and the reaction vessels were heated at 125° C. for 16 hours, cooled and the DMF solution of the quinazolinediones drained into pre-labeled and weighed test tubes. The resin was washed with DMF (0.5 ml) and MeOH (1 ml), collecting the washings, and the test tubes transferred to a SpeedVac and evaporated to dryness. The resulting quinazolinediones were weighed, dissolved in MeCN (2 ml) and analyzed by analytical HPLC and MS for purity and identity.

I claim:

1. A method for the synthesis of 1,3-disubstituted quinazolinedione derivatives which comprises:

(a) reacting a haloformate functionalised polystyrene resin with a substituted anthranilic acid derivative under conditions effective to form a urethane-linkage;

(b) reacting the product of step (a) with a primary amine under conditions effective to form an anthranilamide derivative;

(c) heating the anthranilamide to effect intramolecular cyclisation thereby liberating the 1,3-disubstituted quinazolinedione derivative from the resin into solution; and (d) isolating the 1,3-disubstituted quinazolinedione by filtration and solvent removal.

2. A method as claimed in claim 1 wherein step (a) is effected at between 10° and 50° C.

3. A method as claimed in claim 1 wherein step (b) is effected in the presence of a peptide coupling reagent.

4. A method as claimed in claim 1 wherein step (c) is effected at between 80° and 200° C.

5. A method as claimed in claim 1 wherein the haloformate functionalised polystyrene resin is a chloroformate resin.

6. A method as claimed in claim 5 wherein the chloroformate functionalised polystyrene resin is prepared immediately prior to use from aminomethyl polystyrene resin, triethylene-glycol bischloroformate and Hünig's base.

7. A combinatorial library based upon the quinazolinedione template prepared according to a method as claimed in claim 1.

* * * * *